(12) United States Patent
Baker

(10) Patent No.: US 9,565,852 B2
(45) Date of Patent: *Feb. 14, 2017

(54) METHODS AND REAGENTS FOR MAINTAINING THE VIABILITY OF CANCER CELLS IN SURGICALLY REMOVED TISSUE

(71) Applicant: Truckee Applied Genomics, LLC, San Francisco, CA (US)

(72) Inventor: Tony K. Baker, Truckee, CA (US)

(73) Assignee: Truckee Applied Genomics, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/702,643

(22) Filed: May 1, 2015

(65) Prior Publication Data

US 2015/0230454 A1 Aug. 20, 2015

Related U.S. Application Data

(63) Continuation of application No. 14/211,578, filed on Mar. 14, 2014, now Pat. No. 9,113,623.

(60) Provisional application No. 61/798,627, filed on Mar. 15, 2013.

(51) Int. Cl.
*A01N 1/02* (2006.01)
*C12Q 1/68* (2006.01)
*C12N 5/07* (2010.01)

(52) U.S. Cl.
CPC ........... *A01N 1/0226* (2013.01); *C12Q 1/6806* (2013.01)

(58) Field of Classification Search
CPC ................................ C12N 5/06; C12N 5/0693
See application file for complete search history.

(56) References Cited

U.S. PATENT DOCUMENTS

| | | |
|---|---|---|
| 6,458,546 B1 | 10/2002 | Baker |
| 7,569,342 B2 | 8/2009 | Baker |
| 9,113,623 B2 | 8/2015 | Baker |
| 9,445,586 B2 | 9/2016 | Baker et al. |
| 2001/0007673 A1 | 7/2001 | Goldenberg et al. |
| 2004/0214203 A1* | 10/2004 | Fruehauf .............. C12Q 1/6886 435/6.12 |
| 2008/0064108 A1 | 3/2008 | Baker |
| 2009/0123419 A1* | 5/2009 | Sherman .............. A61K 31/166 424/85.4 |
| 2010/0003748 A1 | 1/2010 | Baker |
| 2010/0086924 A1 | 4/2010 | Donner et al. |
| 2011/0130305 A1 | 6/2011 | Patton et al. |
| 2011/0165611 A1 | 7/2011 | Li et al. |
| 2011/0281754 A1 | 11/2011 | Fischer et al. |
| 2014/0272921 A1 | 9/2014 | Baker |
| 2015/0327539 A1 | 11/2015 | Baker |
| 2016/0235055 A1 | 8/2016 | Baker |

FOREIGN PATENT DOCUMENTS

| | | |
|---|---|---|
| EP | 0797999 A2 | 10/1997 |
| WO | WO-02064166 A1 | 8/2002 |
| WO | WO-2008033936 A2 | 3/2008 |
| WO | WO-2008052170 A2 | 5/2008 |
| WO | WO-2008111981 A1 | 9/2008 |
| WO | WO-2008113017 A2 | 9/2008 |

OTHER PUBLICATIONS

Hassink "Placental Leptin: An Important New Growth Factor in Intrauterine and Neonatal Development" Pediatrics vol. 100 No. 1 Jul. 1997, 1-6.*
Yuen "Circulating Leptin Concentrations Are Positively Related to Leptin Messanger RNA Expression in the Adipose Tissue of Fetal Sheep in the Pregnant Ewe Fed at or Below Maintenance Energy Requirements during Late Gestation" Biology of Reproduction, 67, 911-916 (2002).*
Sigma "RPMI-1640 Media Formulation" Sigma Aldrich, 2016, available at www.sigmaaldrich.com/life-science/cell-culture/learning-center/media-formulations/rpmi-1640.html#rpmi accessed Apr. 22, 2016.*
Gry "Correlations between RNA and protein expression profiles in 23 human cell lines" BMC Genomics, 2009 (10) 365-379.*
Bruno., Apoptotic Pathways are Inhibited by Leptin Receptor Activation in Neutrophils. Journal of Immunology, 2005, 174, 8090-8096.
Co-pending U.S. Appl. No. 14/712,750, filed May 14, 2015.
Notice of allowance dated Jun. 15, 2015 for U.S. Appl. No. 14/211,578.
Office action dated Mar. 26, 2015 for U.S. Appl. No. 14/211,578.
Office action dated Dec. 5, 2014 for U.S. Appl. No. 14/211,578.
Ogunwobi., The anti-apoptotic and growth stimulatory action of leptin in human colon cancer cells involves activation of JNK mitogen activated protein kinase. JAK2 and PI3 kinase/Akt. Int. J. Colorectal Dis. (2007) 22:401-409.
Rouet-Benzineb et al., Leptin Counteracts Sodium Butyrate-induced Apoptosis in Human Colon Cancer HT-29 Cells via NF-KB Signaling. J. Biol. Chem. 279(16): 16495-502. Jan. 29, 2004.
Office action dated Nov. 25, 2015 for U.S. Appl. No. 14/712,750.
Notice of allowance dated Jul. 29, 2016 for U.S. Appl. No. 14/712,750.

(Continued)

*Primary Examiner* — Robert Yamasaki
*Assistant Examiner* — Charles Zoltan Constantine
(74) *Attorney, Agent, or Firm* — Wilson Sonsini Goodrich & Rosati

(57) ABSTRACT

A composition and method for generating reagents and the composition of these reagents for the stabilization and preservation of viability of cancer tissue which has been surgically excised and the suspension and/or termination of apoptosis (cell death) by significant modulation of cell metabolism by low molar concentrations of synergistic chemistries and hormonal growth enhancers while maintaining normal gene expression patterns of the surgically excised tissue.

32 Claims, 8 Drawing Sheets

(56) References Cited

OTHER PUBLICATIONS

Office action dated Apr. 25, 2016 for U.S. Appl. No. 14/712,750.
Office action dated Sep. 8, 2016 for U.S. Appl. No. 15/013,541.
Pierce. Protein stability and storage. Technical Resource. Pierce Biotechnology, USA. Sep. 2005. 3 pages.

* cited by examiner

| Bill of Materials | | | | | | Page 1 |
|---|---|---|---|---|---|---|
| Item | Lot Number | Part Number | Exp Date | Amount per 1000 ml | Amount Used | Operator Checked by |
| Sodium Thiocyanate | | | | 8.1 gm | | |
| 0.1M EDTA | | | | 100 ml | | |
| USP Purified Water (Enter Date for Lot #) | | | | QS 1000 ml | | |
| DMSO | | | | 20 ml | | |
| Glycerol | | | | 25 ml | | |
| K1PO4 Monobasic Potassium Phosphate | | | | 3.93 gm | | |
| K3PO4 Tribasic Potassium Phosphate | | | | 5.02 gm | | |
| Trehalose dihydrate | | | | 7.56 gm | | |
| Leptin | | | | 50 µl | | |

Calculations Performed by _____    Calculations checked by _____

| Text | Data | Operator |
|---|---|---|
| Record the volume prepared | | |
| Date Started | | |
| Expiration Date | | |

1. Assign a 1 year expiration date from the date started

Issued by _____
Date _____
All Pages Attached Yes ___ No ___
Lot # Correct all pages Yes ___ No ___
Expiration date Correct Yes ___ No ___

Documentation Checked By _____    Date Checked _____

Figure 3A

| Text | Data | Operator |
|---|---|---|
| 2. Add 50 ml of USP Purified Water to an appropriate size container.<br><br>                   Time water added<br><br>3. Add 8.1 gm Sodium Thiocyanate and mix until clear.<br><br>                   Mixing start time<br><br>                   Mixing stop time<br>4. Add 100ml of 0.1M EDTA and mix until solution is homogeneous.<br><br>                   Mixing start time<br><br>                   Mixing stop time<br>5. Add 20 ml of DMSO and mix until solution is Homogenous<br>Mixing Start time<br>                   Mixing start time<br><br>                   Mixing stop Time<br><br>6. Add 25ml of Glycerol and mix until solution is homogenous  Mixing Start Time<br><br>                                Mixing Stop Time<br>7. Add 3.93 gm of Monobasic Potassium Phosphate mix until  Mixing Start Time<br>  solution is homogenous                  Mixing Stop time<br>8. Add 5.02 gm grams of K3PO4 Tri Basic potassium Phosphate  Mixing Start Time<br>                                Mixing top time<br><br><br><br>                                Mix start time<br>9. Add 7.65 gm Trehalose dehydrate mix until solution is clear    Mix stop time<br><br>10. Add 50μl Leptin Human   Mix until solution is clear      Mix Start Time<br><br>                                Mix Stop Time<br>11..       ( Label as Follows)<br>      Truckee Applied Genomics<br>      TAG-1 Tissue preservation System<br>       Lot #    Exp Date<br>12. Qs to 1000 ml with DIUF Water | | |
| Reviewed By_____ - Date_____<br>Comments_____ - | | |

Figure 3B

METHODS AND REAGENTS FOR MAINTAINING THE VIABILITY OF CANCER CELLS IN SURGICALLY REMOVED TISSUE

CROSS REFERENCE

The present patent application is a continuation application of nonprovisional patent application Ser. No. 14/211,578 filed on Mar. 14, 2014, which claims the benefit of provisional patent application 61/798,627 filed on Mar. 15, 2013, both of which are herein incorporated by reference.

FIELD

This invention pertains to methods of generating reagents and the composition of reagents for the stabilization, preservation, and viability of cancer tissue which has been surgically excised.

BACKGROUND

Surgical tissue collection for pathology analysis to detect cancer cells from excised tissue has been the standard practice in cancer diagnosis for decades. The current protocols for tissue sample collection call for excised tissue to be collected and placed in a formalin solution, and then transported to the pathology laboratory for staining and analysis. Unfortunately, formalin fixes cells (e.g. kills the cells) and in the process causes significant changes in the cellular integrity which produces problems with the ability to accurately conduct genomic testing (RNA, mRNA and protein biomarker analysis, and gene expression studies) analyses.

Molecular technology, such as genomic testing with real-time polymerase chain reaction technology (qPCR), has evolved to the extent that certain cancers can be matched to specific chemotherapies that have been shown to respond to certain gene expression patterns found in the cancer cells. Thus, being able to obtain accurate gene expression patterns of the cancer cells excised from a patient allows for personalized healthcare by designing individualized chemotherapy as well as other treatments. This is a very important shift in treatment paradigms and will represent the standard of care in the near future.

Cancer tissue samples which have been preserved in formalin are not viable tissue samples for completing gene expression analyses. One reason formalin is not a good reagent for achieving gene expression analysis on tissue samples is that formalin causes the slow cross linking of proteins into a mesh network, and valuable target proteins may be destroyed by the formalin process as they are not protected from degradation.

Furthermore, as formalin penetrates the tissue sample, cell death (apoptosis) occurs. Cancer cells are unique as they have a metabolic pre-programmed apoptosis, thus accelerated apoptosis occurs in formalin. As the cells in the tissue sample die, a subset of the total cell population lyse and release a broad range of internal regulatory enzymes which further cause accelerated cell death. A number of these enzymes will degrade or destroy target nucleic acids, DNA, RNA, mRNA, regulatory proteins, and associated biomarkers used in molecular genomic analysis. During the fixation process, while the formalin kills the cells in the tissue sample, gene expression can become erratic and genomic expression of critical genes can become under expressed or over expressed, giving inaccurate values of the expression of certain cancer genes. This is a major problem when chemotherapy decisions are based on the levels of specific mRNA from selected genes. Thus, accurate genomic testing of cancer cells fixed in formalin is not possible at present.

It should also be noted that fixing the proteins and cells in a tissue sample with formalin takes about 48 hours to occur. Making the formalin process not very exact at determining what the genetic expression is at the time of tissue collection from a patient.

In general, the scientific usefulness of genetic data obtained from tissue fixation is directly related to the quality of the tissue and the usefulness of that tissue for genomic testing. Presently, formalin fixation is not very useful in obtaining accurate genetic expression information. Thus there is a need for reagents for fixing tissue samples, so that the collected sample comprises accurate gene expression markers for genetic testing.

There is also a need for tissue sample fixation reagents that are not as hazardous as formalin. Unfortunately, formalin carries a significant risk of cancer to the users, as well as significant state and federal regulations for the use and disposal of the products containing formalin.

The present invention discloses methods for manufacturing reagents and the composition of reagents which allow for the collection of cancer tissue surgically removed from a patient, in which the genetic cellular information of the cancer cells in the tissue sample are maintained in a viable state, making the tissue sample suitable for genetic expression analysis.

SUMMARY

The present invention discloses novel methods to produce a cell viability reagent for tissue samples such as biopsy samples, which allows for genetic expression analysis of the cells in the sample.

In most embodiments of the methods of producing a reagent for tissue samples, the method comprises providing at least one chaotrope, providing at least one kosmotrope, providing a chelator, providing a buffer, providing an apoptosis substrate, providing a metabolic modulator, and mixing the chaotrope, kosmotrope, chelator, buffer, apoptosis substrate, and the metabolic modulator in such a manner as to enable the gene expression analysis of the tissue sample.

In many embodiments of the methods for producing the reagent for tissue samples, the apoptosis substrate is a cancer cell apoptosis substrate and the tissue sample is a surgically excised cancer tissue.

In most embodiments of the methods of the invention, the final concentration of the chaotrope is from about 0.1 molar (0.1 M) to about 2 M, the kosmotrope is from about 0.1 M to about 2 M, the chelator is from about 0.1 M to about 2 M, and the apoptosis substrate is from about 0.001 M to about 0.5 M in the reagent for tissue samples.

In certain embodiments of the methods of the invention, the chaotrope is selected from the group consisting of SCN (sodium thiocyanate), $H_2PO_4^-$, $HCO_3^-$, $I^-$, $Cl^-$, $NO_3^-$, $NH_4^+$, $Cs^+$, $K^+$, $(NH_2)_3C^+$, guanidinium, all salts of guanidinium, $Br^-$, or $Rb^+$.

In some embodiments of the method of making the reagent, the at least one kosmotrope is selected from the group consisting of Glycerol, Trimethylamine N-oxide, Ectoine, α,α-Trehalose, 3-Dimethylsulfoniopropionate, Glucose, Dextran, or D-Lactose.

In other embodiments the chelator is selected from the group consisting of EDTA, EGTA, or BAPTA.

In another embodiment of the methods of the invention, the buffer is selected from the group consisting of BIS-TRIS, BIS-TRIS Propane, HEPES, HEPES Sodium Salt, MES, MES Sodium salt, MOPS, MOPS sodium salt, sodium salt or sodium phosphate buffer (monobasic, tribasic $PO_4$).

In yet another embodiment of the method, the apoptosis substrate is selected from the group consisting of DMSO, Leptin, Glycine betaine, potassium citrate, Trimethylamine, proline, NDSB 195, L-Arginine, Xylitol, Sodium selenite, NDSB 201, $CuCl_2$, or CTAB.

In some embodiments the metabolic modulator is selected from the group consisting of polar aprotic solvents, DMSO, Acetone, N,N-Dimethylformamide, or Acetonitrile.

In most embodiments, the methods of producing the reagent further comprise adding the various components of the reagent to an aliquot of purified water in the sequential order of adding at least one chaotrope, followed by the addition of the chelator, followed by the addition of the metabolic modulator, followed by the addition of a first kosmotrope, followed by the addition of the buffer, followed by the addition of a second kosmotrope which is different from the first kosmotrope, and finally followed by the addition of the apoptosis substrate.

In many embodiments of the invention the chaotrope is $SCN^-$ (sodium thiocyanate), the first kosmotrope is glycerol and the second kosmotrope is α,α-Trehalose, the chelator is EDTA, the buffer is Sodium Phosphate Buffer (monobasic, tribasic $PO_4$), the cell apoptosis substrate is leptin, and the metabolic modulator is DMSO.

In another embodiment the method of manufacturing a reagent for analyzing tissue samples comprises providing an aliquot of purified water, adding components of the reagent to the purified water in the following order: adding sodium thiocyanate, EDTA, DMSO, glycerol, potassium phosphate buffer, and α,α-Trehalose, followed by adding human leptin and mixing the components between each addition of the various components in a manner that allows for accurate genetic expression analysis of the tissue sample or biopsy.

In some embodiments the method of manufacturing a reagent for analyzing tissue samples comprises providing an aliquot of purified water, adding components of the reagent to the purified water in the following order: adding at least one chaotrope, followed by the addition of a chelator, followed by the addition of a metabolic modulator, then adding a first kosmotrope, then adding a buffer, followed by adding a second and different kosmotrope, followed by adding an apoptosis substrate, and mixing the components between each addition of components in a manner that allows for accurate genetic expression analysis of the tissue sample.

In most embodiments the reagent for preparing tissue samples which allows for genetic expression analysis comprises at least one chaotrope, at least one kosmotrope, a chelator, a buffer, an apoptosis substrate, and a metabolic modulator.

For analyzing cancer tissue samples, the apoptosis substrate is a cancer cell apoptosis substrate.

For most embodiments of the reagent, the final concentration for the chaotrope is from about 0.1 M to about 2 M, the at least two kosmotropes are from about 0.1 M to about 2 M for each kosmotrope, the chelator is from about 0.1 M to about 2 M, and the apoptosis substrate is from about 0.001 M to about 0.5 M.

In specific embodiments of the reagent, the chaotrope is $SCN^-$ (sodium thiocyanate), the kosmotropes are glycerol and α,α-Trehalose, the chelator is EDTA, the buffer is Sodium Phosphate Buffer (monobasic, tribasic $PO_4$), the cell apoptosis substrate is leptin, and the metabolic modulator is DMSO.

In some embodiments of the reagent the chaotrope is selected from the group consisting of SCN (sodium thiocyanate), $H_2PO_4^-$, $HCO_3^-$, $I^-$, $Cl^-$, $NO_3^-$, $NH_4^+$, $Cs^+$, $K^+$, $(NH_2)_3C^+$, guanidinium, all salts of guanidinium, $Br^-$, or $Rb^+$.

In yet other embodiments of the reagent, the kosmotrope is selected from the group consisting of Glycerol, Trimethylamine N-oxide, Ectoine, α,α-Trehalose, 3-Dimethylsulfoniopropionate, Glucose, Dextran, or D-Lactose.

In yet another embodiment of the reagent the chelator is selected from the group consisting of EDTA, EGTA, or BAPTA.

The preserving reagent in some embodiments comprises a buffer which is selected from the group consisting of BIS-TRIS, BIS-TRIS Propane, HEPES, HEPES Sodium Salt, MES, MES Sodium salt, MOPS, MOPS Sodium Salt, Sodium salt or Sodium Phosphate Buffer (monobasic, tribasic $PO_4$).

In other embodiments of the reagent, the apoptosis substrate is selected from the group consisting of DMSO, Leptin, Glycine betaine, potassium citrate, Trimethylamine, proline, NDSB 195, L-Arginine, Xylitol, Sodium selenite, NDSB 201, $CuCl_2$, or CTAB.

While yet another embodiment of the reagent comprises the metabolic modulator being selected from the group consisting of polar aprotic solvents, DMSO, Acetone, N,N-Dimethylformamide, or Acetonitrile.

All patents and publications identified herein are incorporated by reference in their entirety.

BRIEF DESCRIPTION OF THE FIGURES

FIGS. 3A and 3B are a formulation sheet showing one embodiment of the components of a reagent used for preserving tissue samples and the sequential addition of each component in accordance with the invention.

DESCRIPTION

Figure 1:
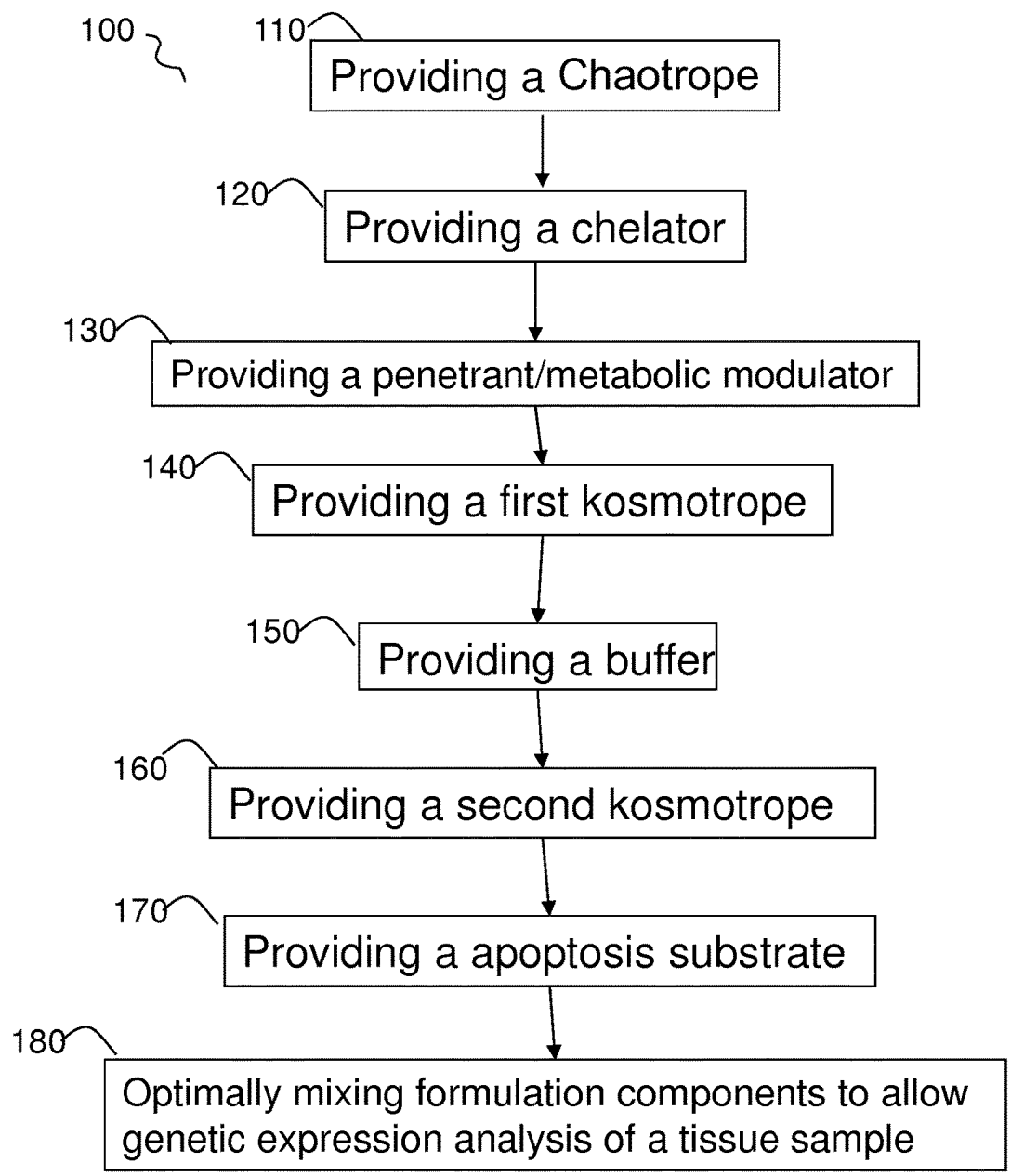
FIG. 1 is a flow chart showing one embodiment of the method of producing a reagent for surgically removed tissue, which allows for genetic expression analysis of the tissue sample in accordance with the invention.

Unless otherwise stated, the following terms used in this application, including the specification and claims, have the definitions given below. It must be noted that as used in the specification and the appended claims, the singular forms "a," "an," and "the" include plural referents unless the context clearly dictates otherwise.

"Optional" or "optionally" means that the subsequently described event or circumstance may but need not occur, and that the description includes instances where the event or circumstance occurs and instances in which it does not.

The terms "those defined above" and "those defined herein" when referring to a variable incorporates by reference the broad definition of the variable as well as preferred, more preferred, and most preferred definitions, if any.

The term chaotrope refers to compounds that interact weakly with water molecules and disrupt the water molecule hydrogen bonded network around protein molecules.

The term kosmotrope refers to compounds that interact strongly with water molecules, and organize water molecules in a typically favorable manner around protein molecules. A biomaterial stabilizing composition may include a kosmotrope in some embodiments. Without being limited to any specific mechanism(s) of action, a kosmotrope, in some embodiments, may stabilize and/or improve water-water interactions in an aqueous composition. Examples of kosmotropes may include, without limitation, glycerol, proline (e.g., L-proline), trehalose (e.g., D-(+) trehalose, D-(+) trehalose dihydrate), α,α-Trehalose, glycine betaine, glucose, dextrose, glutamic acid, and/or aspartic acid. Examples of a kosmotrope, in some embodiments, may include $SO_4^-$, $HPO_4^-$, $Ca^{2+}$, $Mg^{2+}$, $Li^+$, $Na^+$, $OH^-$, and/or $PO_4^{2-}$.

The term buffer refers to compound which gives a mixture a pH from about 4.5 to about 8.5. In some embodiments, a suitable buffer may be selected from Good buffers (e.g., HEPES), potassium acetate, sodium phosphate, potassium bicarbonate, tris(hydroxyamino)methane (Tris), and combinations thereof. For example, a buffer may include potassium acetate, sodium acetate, potassium phosphate (mono, tribasic), sodium phosphate, Tris, N-(2-hydroxyethyl)piperazine-N'-(2-ethanesulfonic acid) (HEPES) buffer, 3-(N-morpholino)propane sulfonic acid (MOPS) buffer, 2-[(2-amino-2-oxoethyl)amino]ethanesulfonic acid (ACES) buffer, N-(2-acetamido)-2-iminodiacetic acid buffer (ADA), 3-[(1,1-dimethyl-2-hydroxyethyl)amino]-2-propanesulfonic acid (AMPSO) buffer, N,N-bis(2-hydroxyethyl)-2-aminoethanesulfonic acid (BES) buffer, Bicine (N,N-bis(2-hydroxyethylglycine) buffer, bis-(2-hydroxyethyl)imino-tris (hydroxymethyl)methane (Bis-Tris) buffer, 3-(cyclohexylamino)-1-propanesulfonic acid (CAPS) buffer, 3-(cyclohexylamino)-2-hydroxy-1-propanesulfonic acid (CAPSO) buffer, 2-(N-cyclohexylamino)ethanesulfonic acid (CHES) buffer, 3-[N,N-bis(2-hydroxyethyl)amino]-2-hydroxy-propanesulfonic acid (DIPSO) buffer, N-(2-hydroxyethylpiperazine)-N'-(3-propanesulfonic acid) (HEPPS) buffer, N-(2-hydroxyethyl)piperazine-N'-(2-hydroxypropanesulfonic acid) (HEPPSO) buffer, 2-(N-morpholine)ethanesulfonic acid (MES) buffer, triethanolamine buffer, imidazole buffer, glycine buffer, ethanolamine buffer, phosphate buffer, 3-(N-morpholine)-2-hydroxypropanesulfonic acid (MOPSO) buffer, piperazine-N,N'-bis(2-ethanesulfonic acid) (PIPES) buffer, piperazine-N,N'-bis(2-hydroxypropanesulfonic acid) (POPSO) buffer, N-tris[(hydroxymethyl)methyl]-3-aminopropanesulfonic acid (TAPS) buffer, 2-hydroxy-3-[tris(hydroxymethyl)methylamino]-1-propanesulfonic acid (TAPSO) buffer, N-[Tris(hydroxymethyl)methyl]-2-aminoethanesulfonic acid (TES) buffer, N-[Tris(hydroxymethyl)methyl]glycine (tricine) buffer, 2-amino-2-methyl-1,3-propanediol buffer, 2-amino-2-methyl-1-propanol buffer, and combinations thereof.

The term chelator refers to a compound that may bind available metals (e.g., $Mg^{2+}$ and $Ca^{2+}$) to such an extent that metals that remain available to the metal-dependent enzymes (e.g., deoxyribonucleases) are insufficient to support catalysis (i.e., nucleic acid degradation). For example, a metal independent enzyme may include a DNA ligase (e.g., D4 DNA ligase), a DNA polymerase (e.g., T7 DNA polymerase), an exonuclease (e.g., exonuclease 2, lamda-exonuclease), a kinase (e.g., T4 polynucleotide kinase), a phosphotase (e.g., BAP and CIP phosphotase), a nuclease (e.g., BL31 nuclease and XO nuclease), and an RNA-modifying enzyme (e.g., RNA polymerase, SP6, T7, T3 RNA polymerase, and T4 RNA ligase).

A chelator may include, for example, ethylenediaminetetraacetic acid (EDTA), [ethylenebis(oxyethylenenitrilo)]tetraacetic acid (EGTA) and 1,2-bis(2-aminophenoxy)ethane-N,N,N',N'-tetraacetic acid (BAPTA), and/or salts thereof. A chelator may be present at any desirable concentration. Where two or more chelators are included in a single reagent, either the concentration of each chelator or the total concentration of the combined chelators may fall within any of the provided ranges. In some embodiments, a chelator may include EDTA, EGTA, BAPTA, imidazole, iminodiacetate (IDA), bis(5-amidino-2-benzimidazolyl)methane (BABIM), and/or salts thereof.

The term metabolic modulator refers to penetrants/metabolic modulators that act to optimize membrane penetration of chemistries within the reagent formulation, as well as stabilizing gene expression of cells, and in particular, hypoxic cancer cells.

The term apoptosis is the process of programmed cell death (PCD) that may occur in multicellular organisms. Biochemical events lead to characteristic cell changes (morphology) and death. These changes include blebbing, cell shrinkage, nuclear fragmentation, chromatin condensation, and chromosomal DNA fragmentation. (See also apoptotic DNA fragmentation).

The term "apoptosis substrate" is a compound or molecule which is a key component in the reduction of apoptosis. An apoptosis substrate works synergistically with other reagent formulation components to prevent apoptosis and foster cell stability and cell growth.

The term "genetic expression analysis" refers to analyses that deal with detecting the over expression, under expression or differentially expressed genes of a cell, particularly in cancer cells.

The terms "overexpress," "overexpression," or "overexpressed" interchangeably refer to a protein or nucleic acid (RNA) that is translated or transcribed at a detectably greater level, usually in a cancer cell, in comparison to a normal cell. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR (reverse transcriptase-PCR), PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold, or higher levels of transcription or translation in comparison to a normal cell.

The terms "underexpress," "underexpression," or "underexpressed" or "downregulated" interchangeably refer to a protein or nucleic acid that is translated or transcribed at a detectably lower level in a cancer cell, in comparison to a normal cell. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-fold, 2-fold, 3-fold, 4-fold, or lower levels of transcription or translation in comparison to a control.

The term "differentially expressed" or "differentially regulated" refers generally to a protein or nucleic acid that is overexpressed (upregulated) or underexpressed (downregulated) in one sample compared to at least one other sample, generally in a cancer patient compared to a sample of non-cancerous tissue in the context of the present invention.

The term "tumor" as used herein refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, and brain cancer.

Biological or tissue sample includes sections of tissues such as biopsy and autopsy samples. A biological sample is typically obtained from a eukaryotic organism, most preferably a mammal such as a primate (e.g., chimpanzee or human), cow, dog, cat, a rodent (e.g., guinea pig, rat, or mouse), rabbit, or a bird, reptile, or fish.

A biopsy refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., lung etc.), the size and type of the tumor, among other factors. Representative biopsy techniques include, but are not limited to, excisional biopsy, incisional biopsy, needle biopsy, surgical biopsy, and bone marrow biopsy. An excisional biopsy refers to the removal of an entire tumor mass with a small margin of normal tissue surrounding it. An incisional biopsy refers to the removal of a wedge of tissue from within the tumor. A diagnosis or prognosis made by endoscopy or radiographic guidance can require a "core-needle biopsy" or a "fine-needle aspiration biopsy" which generally obtains a suspension of cells from within a target tissue.

Therapeutic treatment and cancer therapies refer to chemotherapy, hormonal therapy, radiotherapy, immunotherapy, and biologic (targeted) therapy.

The term PCR refers to polymerase chain reaction. This refers to any technology where a nucleotide is amplified via temperature cycling techniques in the presence of a nucleotide polymerase, preferably a DNA polymerase. This includes but is not limited to real-time PCR (qPCR) technology, reverse transcriptase PCR (RT-PCR), and standard PCR methods.

The present invention discloses methods for manufacturing a reagent for maintaining cellular viability of tissue samples which enables the analysis of genetic expression of the cells in the tissue sample. The present invention also relates to reagent compositions which allow for the testing of accurate gene expression of viable cells in tissue samples, particularly cancer cells. The methods for making the cell viability reagent, in general, have a sequential addition of compounds/molecules to achieve the optimum formulation of the reagent of the invention.

Referring to FIG. 1, there is a flow chart of one embodiment of the methods of manufacturing a cell viability reagent in accordance with the invention. The method 100 for generating a cell viability reagent comprises providing a chaotrope at event 110. The chaotrope is added to an aliquot of purified water. The chaotrope is a molecule which has activity against enzymes that degrade nucleic acids such as DNAases and RNAases, proteases, and regulatory enzymes responsible for protein destruction and apoptosis. A chaotrope also has significant effects on water distribution in cells and associated metabolic attenuation.

In most embodiments, the chaotrope is at least one of the following compounds; $SCN^-$(sodium thiocyanate), $H_2PO_4^-$, $HCO_3^-$, $I^-$, $Cl^-$, $NO_3^-$, $NH_4^+$, $Cs^+$, $K^+$, $(NH_2)_3C^+$, guanidinium, all salts of guanidinium, $Br^-$, or $Rb^+$. All of these compounds are known to have effects on water distribution around a cell and help in maintaining cell viability.

In some embodiments, the chaotrope has a final concentration in the cell viability reagent of concentrations ranging from about 0.1 M to about 2 M, more preferably from at least about 1 mM, at least about 10 mM, at least 0.05 M, at least about 0.1 M at least 0.5 M at least about 1 M, at least about 1.75 M, at least about 2 M, to a maximum of at least about 3 M.

At event 120, method 100 comprises providing at least one chelator. The chelator is added to the cell viability formulation to help in the inactivation of $Ca^{2+}$, $Mg^{2+}$, driven enzyme systems that degrade nucleic acids. In this embodiment, the chelator is selected from the following group of compounds: EDTA, EGTA, or BAPTA.

In most embodiments of the method of formulating the cell viability reagent, the chelator is found at a final concentration of about 0.1 M to about 2 M, more preferably from about at least about 0.1 M, at least about 0.005 M, at least about 0.01 M, at least about 0.05 M, and/or at least about 0.1 M.

At event 130, the method 100 further comprises providing a metabolic modulator/penetrant compound. The metabolic modulator acts to optimize membrane penetration of chemistries as well as acting as a carrier for large molecules such as glycerol. Additionally, it acts as a profound modulator of cell differentiation and function. The metabolic modulator is a key component in stabilizing gene expression of hypoxic cancer cells.

In the method 100, the metabolic modulator/penetrant is selected from the group consisting of polar aprotic solvents, DMSO, Acetone, N,N-Dimethylformamide, or Acetonitrile. The final concentration of the metabolic modulator in the formulations is from at least 0.25 M, at least about 0.5 M, at least about 0.75 M. at least about 1 M, at least about 1.5 M, to a maximum of about 2 M.

The method 100 further comprises providing at least one kosmotrope for manufacturing the cell viability reagent at event 140. In this embodiment the kosmotrope(s) is added to the mixture after the addition of the chaotrope. The kosmotrope(s) maybe one of the following compounds: Glycerol, Trimethylamine N-oxide, Ectoine, α,α-Trehalose, 3-Dimethylsulfoniopropionate, Glucose, Dextran or D-Lactose. The kosmotrope(s) has protective effects for nucleic acids, proteins and protein folding, and is a necessary component of the reagent that synergizes with chaotropes for cell and membrane stability and metabolic modulation for stabilization of gene expression when cells are stressed.

In some embodiments that kosmotrope is found in a final concentration of the cell viability reagent in concentrations ranging from about 0.1 M to about 2 M, or from about 0.1 mM to about 100 mM, from about 1 mM to about 10 mM, from about 0.1 M about 1.0 M to about 2.0 M, from about 0.1 M to about 5.0 M.

At event 150, method 100 comprises providing for at least one buffer which is added to the formulation to adjust the pH of the cell viability reagent. The buffer in most embodiments is selected from the group consisting of BIS-TRIS, BIS-TRIS Propane, HEPES, HEPES sodium salt, MES, MES sodium salt, MOPS, MOPS Sodium Salt, Sodium salt or Sodium Phosphate Buffer (monobasic, tribasic $PO_4$).

In most embodiments, the final pH of the cell viability reagent is from about 4.5 to about 8, more preferably from about 5.0 to about 5.5 to about 5.5 to 6.0, to about 6.5, to about 7.0 to about 7.5.

The method 100 further comprises providing a second kosmotrope for manufacturing the cell viability reagent at event 160. In this embodiment the kosmotrope(s) is added to the mixture after the addition of the buffer. The kosmotrope(s) maybe one of the following compounds: Glycerol, Trimethylamine N-oxide, Ectoine, α,α-Trehalose, 3-Dimethylsulfoniopropionate, Glucose, Dextran, or D-Lactose. The kosmotrope(s) has protective effects for nucleic acids, proteins and protein folding, and is a necessary component of the reagent that synergizes with chaotropes for cell and membrane stability and metabolic modulation for stabilization of gene expression when cells are stressed.

In some embodiments that kosmotrope is found in a final concentration of the cell viability reagent in concentrations ranging from about 0.1 M to about 2 M, more preferably from about 0.1 mM to about 100 mM, from about 1 mM to about 10 mM, from about 0.1 M about 1.0 M to about 2.0 M, from about 0.1 M to about 5.0 M.

The method 100 further comprises providing an apoptosis substrate at event 170. An apoptosis substrate aids in the prevention of apoptosis of cells, and in particular cancer cells. The apoptosis substrate is selected from the group consisting of DMSO, Leptin, Glycine betaine, potassium citrate, Trimethylamine, proline, NDSB 195, L-Arginine, Xylitol, Sodium selenite, NDSB 201, $CuCl_2$, or CTAB.

The final concentration of the apoptosis substrate in the cell viability reagent is from about 0.001 M to about 0.5 M, or from about 0.1 mM, up to about 1 mM, up to about 10 mM, up to about 0.1 M, up to about 0.25 M, up to about 1 M, up to 1.5 M up to a maximum of about 2 M.

At event 180, the method of 100 further provides mixing the chaotrope, kosmotrope, chelator, buffer, apoptosis substrate, and the metabolic modulator to enable the gene expression analysis of the tissue sample. The mixing of the samples may happen throughout the method of formulating the reagent of the invention. Each individual component is treated and mixed to obtain the optimal cell viability reagent. The addition of the components of the formulation maybe random; however, in most embodiments the addition of the components is sequential in the order shown in method 100.

The preparation time for producing the reagent varies due to the batch size, temperature, etc. In general, it takes approximately one hour to complete the formulation of the cell viability reagent. The reagent maybe stored at ambient conditions for up to 12 months prior to use on tissue samples. The reagent may also be frozen for longer storage.

Once a tissue sample has been added to the cell viability reagent, the tissue is stabilized and maintains viable gene expression components for up to 72 hours at 30° C. temperature. In general, the time the cells are viable is about 30 hours to about 50 hours and more particularly about two days. This time frame is sufficient for detailed genetic expression analysis of tissues from biopsies (tissue samples) that can give significant insight into the types and progression of diseases such as cancer.

Figure 2:
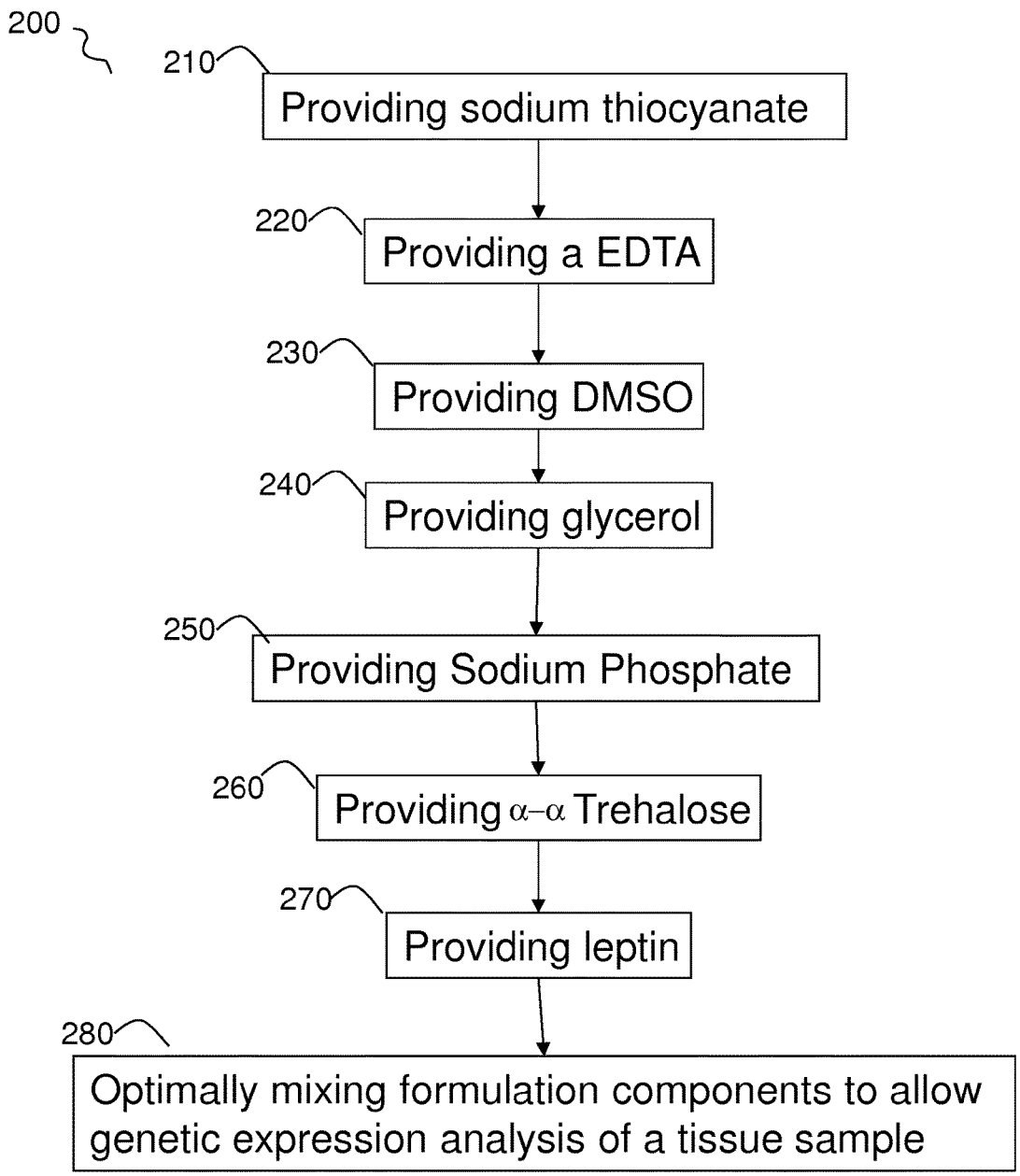
FIG. 2 is a flow chart showing one embodiment of the method of manufacturing a reagent for surgically removed tissue, particularly cancerous tissue, which allows for genetic expression analysis of the tissue sample in accordance with the invention.

Referring to FIG. 2, there is a flow chart showing an embodiment of the methods for generating the cell viability reagent in accordance with the invention. The method 200 comprises providing Sodium thiocyanate at event 210. Sodium thiocyanate is a chaotrope and is added to purified water and mixed thoroughly before adding the chelator EDTA at event 220. After the mixing of the EDTA into the solution, the metabolic modulator/penetrant DMSO (Dimethylsulfoxide) is added to the mixture at event 230.

At event 240 a first kosmotrope, glycerol, is added to the formulation of the reagent. The formulation is mixed until the solution is clear and then the buffer component of the reagents is added in event 250. The buffer of the method showing in FIG. 2 is Sodium Phosphate Buffer (monobasic, tribasic $PO_4$). This buffer ensures that the pH of the final cell viability reagent will be around about 7.0 to 7.6 and more likely around 7.2.

At event 260, a second kosmotrope, different from the first kosmotrope is added to the formulation. The second kosmotrope in method 200 is α,α-Trehalose.

At event 270, the method of 200 further comprises adding leptin and an apoptosis substrate which helps in the prevention of cellular apoptosis, particularly of cancerous cells.

At event 280, the method 200 further provides mixing of the components of the reagent formulation. After each component addition, mixing is completed to ensure the each component is solubilized within the reagent solution.

TABLE I

| Cell Viability study 1 day (24 hours) | Cellular Clumps | Trypan Blue Viability | Viability/ Proliferation MTT |
|---|---|---|---|
| TAG-1 | No Cell Clumps | No Dead Cells | 100% |
| TAG-2 | Few Cell Clumps | Many Dead Cells | 53% |
| Formalin | Cell Destroyed | All Cells Dead | 0% |

Table I, above, shows the viability of Ishikawa cancer cells after one day of being exposed to one embodiment of the preserving reagent with and without leptin added to the reagent, TAG-1 and TAG-2, respectively. TAG-1 and TAG-2, in Table 1 are compared to the viability of the Ishikawa cancer cells when they are place in a 20% buffered formalin solution. TAG-1 in Table I comprises Sodium Thiocyanate, EDTA, buffers, α,α-Trehalose, DMSO, Glycerol and Leptin. TAG-2 solution shown in Table 1 comprises the same components of TAG-1 but without the presence of Leptin.

Table 1 shows the viability of the cancer cells by measuring the presence of cellular clumps in the solutions, trypan blue results for indication of the presence of dead cells and the viability/proliferation of the cells using MTT. The MTT assay is a colorimetric assay for assessing cell viability NAD(P)H-dependent cellular oxidoreductase enzymes under defined conditions which reflects the number of viable cells present. These enzymes are capable of reducing the tetrazolium dye to its insoluble formazan which has a purple color. Dead cells do not cause this color. The MTT dye is added to cell suspensions and read at a spectrophometric setting of 570 nm and a background wavelength 630/690 nm. The density of viable cells and growing cells proliferation are calculated using a ratio of dead cells (yellow color) to live cells (purple color) on a defined grid. The results shown in Table I indicate that at 24 hours exposure to the preserving reagents, TAG-1 has 100% viability, TAG-2 has 53% viability and the formalin solution has 0% cellular viability.

TABLE II

| Cell Viability study 8 days (192 hours) | Cellular Clumps | Trypan Blue Viability | Viability/ Proliferation MTT |
|---|---|---|---|
| TAG-1 | Few Cell Clumps | Few Dead Cells | 88.94% |
| TAG-2 | Diffuse Cell Clumps | >95% Dead Cells | 5% |
| Formalin | Cell Destroyed | All Cells Dead | 0% |

Table II, above, shows the viability of the Ishikawa cancer cells after being exposed to TAG-1, TAG-2 or the formalin preserving solutions for eight days. The preserving reagents of the invention, TAG-1 and TAG-2, are the same as those used in the experiment shown in Table I. After eight days of exposure to the preserving reagents at room temperature, TAG-1 has a viability of 88.94%, TAG-2 has a cell viability of 5%, and in the formalin solution, all the cells were dead. These results indicate that the preserving reagent(s) of the invention is much better at preserving cell viability over time than formalin. These results also demonstrate the importance of adding leptin as an apoptosis component.

When the reagent is prepared correctly it can act as a cancer tissue preservative, maintaining cell viability in the tissue with a 95% viability for up to 24 hours. Viability from one to about five days can be achieved with an average viability of about three days. The reagent also aids in the inhibition or significant suppression of cancer cell apoptosis in tissue, controls cellular factors such as hypoxia, and helps in the rapid inactivation of degrading enzymes to protect tissue and nucleic integrity.

Furthermore, approximately 90% tissue penetration is seen within two hours and the rapid buffering of the chemistry components to a pH of 7.2 allows for maximum cellular metabolic activity of the reagent components. The reagent of the invention allows for modulation of cellular metabolic stress by biochemical mechanisms utilizing chaotropic, kosmotropic chemistries, buffering systems, and a novel cancer-stimulating hormone leptin which has been shown to increase the growth of cancer in obese patients. Adding a cryoprotectant such as glycerol which may act as a kosmotrope for protein preservation, may also impart thermo stability to the tissue specimen.

Another benefit of the reagent is that the reagent stabilizes gene expression of target RNA and mRNA, measured by real time PCR or microarray methods. Rapid penetration of reagent components into cells and tissue has been observed.

TABLE III

| Formulation Chemistry | RIN control 0 hours | RIN 24 hours | RIN 72 hours | RIN 120 hours | RIN 170 hours |
|---|---|---|---|---|---|
| TAG-1 | 8.7 | 8.2 | 7.9 | 7.4 | 6.0 |
| TAG-2 | 5.1 | 2.7 | 1.5 | 1.1 | 0 |
| TAG-3 | 6.7 | 3.1 | 1.6 | 1.3 | 0 |
| TAG-4 | 7.2 | 2.5 | 2.4 | 1.8 | 0 |
| TAG-5 | 5.8 | 4.2 | 1.3 | 0 | 0 |

Table III show the results of a RNA integrity study comparing five different formulations of the cellular preserving reagent of the invention. Ishikawa cancer cells were exposed or aged in the various formulations for up to 170 hours prior to extracting RNA from the cells. The TAG-1 formulation comprises leptin and $\alpha,\alpha$-Trehalose, Sodium Thiocyanate, EDTA, buffers, DMSO, and glycerol. TAG-2 formulation had no $\alpha,\alpha$-Trehalose or leptin present. TAG-3 formulation had no glycerol, leptin or $\alpha,\alpha$-Trehalose added. TAG-4 formulation had no DMSO, buffers or leptin. TAG-5 formulation had no Leptin, $\alpha,\alpha$-Trehalose, sodium Thiocyanate or EDTA.

The Ishikawa cancer cells utilized in the study shown in Table III are endometrial adenocarcinoma cells which were grown in DMEM media, supplemented with 5% bovine serum. The cells were seeded at a density of $1 \times 10^6$ on a 100 mm tissue culture dish. The cells were harvested using traditional methods and then resuspended in various formulations of the cell preserving reagent of the invention and left at room temperature for various amounts of time. At various time points the cellular RNA was extracted using an RNeasy™ mini kit and the RNA was analyzed for quality and quantity using the Agilent 2000 Bioanalyzer using the manufacturer's standard protocols. Controls for this study were archived purified cellular RNA.

The results shown on Table III indicate that the preferred embodiment of the invention comprises all of the elements shown in FIG. 2. The need for $\alpha,\alpha$-Trehalose and Leptin in the cell preserving formulation of the invention is clearly shown in Table III. The RNA Integrity Number (RIN) measured by the Agilent 2000 RNA analyzer has a scale from 1 to 10. Any number below 6 is considered to show degraded and unreliable RNA which is not useful for gene expression studies. TAG-1 is the only formulation that has a RIN number that stays above 6.0, even at the 170 hour time point. The final concentrations of the TAG-1 formulation embodiment of the invention was; Sodium Thiocyanate 0.01 M, EDTA 0.01 M, Glycerol 0.25 M, Buffers 0.001 M, Leptin 0.001 M, $\alpha,\alpha$-Trehalose 0.20 M.

The reagent of the invention is also compatible with standard staining pathology methods. Cells were treated in the TAG-1 reagent for 24 hours and stained with Hematoxylin and Eosin stain using standard protocols. The stained cells were compared with untreated cells which were also stained with hematoxylin Eosin stain using the same standard protocols. The cells were examined microscopically for cytoplasmic, nuclear, and extracellular matrix features. In both cell sets nuclei stained blue, whereas the cytoplasm and extracellular matrix had consistent pink staining. In summary there were no significant differences with staining of TAG-1 treated cells and cells not treated with TAG-1 chemistry.

In most embodiments, the cell viability reagent comprises a chaotrope, at least one kosmotrope, a chelator, a buffer, a metabolic modulator, and an apoptosis substrate. These components of the reagent are found in low molar concentrations compared to other tissue preservatives. Low molar concentrations of chaotropes act very differently and demonstrate a very protective effect on the stability and preservation of nucleic acids, as well as having a major impact on cell metabolism by modifying water distribution and metabolism of cells as described herein. Basis for U.S. Pat. No. 6,458,546 B1 (Baker). The final concentrations for the chaotrope is from about 0.1 M to about 2 M, the at least two kosmotropes are from about 0.1 M to about 2 M for each kosmotrope, the chelator is from about 0.1 M to about 2 M, and the apoptosis substrate is from about 0.001 M to about 0.5 M. Unlike high molar concentrations of chaotropes which destroy cells and denature proteins and nucleic acids, lower concentration of the chaotropes have been shown to be beneficial in preserving tissue samples. Also, low molar concentrations of kosmotropes are very synergistic with low concentrations of chaotropes in modifying cellular metabolism, protecting proteins and nucleic acids. Optimum stabilization of biological macromolecules (e.g. cancer cells) requires a mixture of one or more kosmotropic anions and a chaotropic action from one of the following groups.

In certain embodiments, the chaotrope is $SCN^-$ (sodium thiocyanate), the kosmotropes are glycerol and α,α-Trehalose, the chelator is EDTA, the buffer is sodium phosphate buffer (monobasic, tribasic $PO_4$), the cell apoptosis substrate is leptin, and the metabolic modulator is DMSO.

The invention also provides kits for biopsy samples which comprise a vessel, the vessel configured to hold a cell viability reagent, wherein the cell viability reagent allows for genetic expression analyses of the biopsy sample.

In most embodiments, the vessel in the kit is a cup or tube of ample size to hold a biopsy tissue sample, as well as an aliquot of the reagent of the invention. The tube maybe an eppendorf tube or larger depending on the size of the tissue sample to be analyzed. The reagent in the kit comprises at least one chaotrope, at least one kosmotrope, a chelator, a buffer, an apoptosis substrate, and a metabolic modulator.

In other embodiments, the cup comprises a lid for sealing the cell viability reagent in the cup.

Preferred methods for manufacturing a cell viability reagent for tissue samples, especially cancer tissue samples, are provided in the following examples.

EXAMPLES

The following preparations and example are given to enable those skilled in the art to more clearly understand and to practice the present invention. They should not be considered as limiting the scope of the invention, but merely as being illustrative and representative thereof.

Example I

This example is a demonstration of one embodiment of the methods for producing the reagent for maintaining cellular viability of a tissue sample. FIGS. 3A and 3B are pictures of a formulation sheet listing the components of the reagent and instructions on how to prepare the cellular viability reagent for tissue biopsy samples. In this example one liter of reagent is made. The components on the formulation sheet are listed in the order they are to be added except for the purified water which is measured out initially (50 mL). The chaotrope, 8.1 g of sodium thiocyanate, is added to the water to give a final concentration of sodium thiocyanate of 10% w/v. The sodium thiocyanate is mixed until the solution is clear. Following the addition of the chaotrope, EDTA, the chelator, is added to the solution at a stock concentration of 0.1 M. 100 mL of 0.1 M EDTA is added to give a final concentration of 0.01 M EDTA in the reagent. The EDTA is mixed until the solution is homogeneous. The next component added to the solution is the metabolic modulator, DMSO. DMSO (20 mL) is added to the solution to give the final percentage of 2% DMSO in the reagent. After adding the DMSO, the solution is mixed until it is homogeneous. The first kosmotrope, glycerol (25 mL) is then added to the solution giving the final percentage of glycerol in the reagent of 2.5%. The solution is mixed again until homogeneous. The buffering components are then added to the solution. $KH_2PO_4$ (3.93 g), monobasic potassium phosphate, is added first and mixed to homogeneity, followed by the addition of 5.02 g of $K_3PO_4$, tribasic potassium phosphate. Once the solution is homogeneous, the second kosmotrope, α,α-Trehalose dihydrate is added to the solution. α,α-Trehalose dihydrate (7.56 g) is added to the reagent. The solution is then mixed until clear. The final component added to the solution is the apoptosis substrate, human leptin. 50 microliters (0.001 M) of leptin is added to the solution which is then mixed until clear.

Purified water is then added to bring the volume up to one liter. All of the steps above are carried out a room temperature. The cellular viability reagent can be stored for up to one year under ambient conditions.

The formulation sheet of FIGS. 3A and 3B, as well as this example, is an excellent representation of one embodiment of the methods in producing the viable cell tissue reagent as well as a good example of the components which comprise a viable cell tissue reagent in accordance of the invention.

Example II

Figure 4:
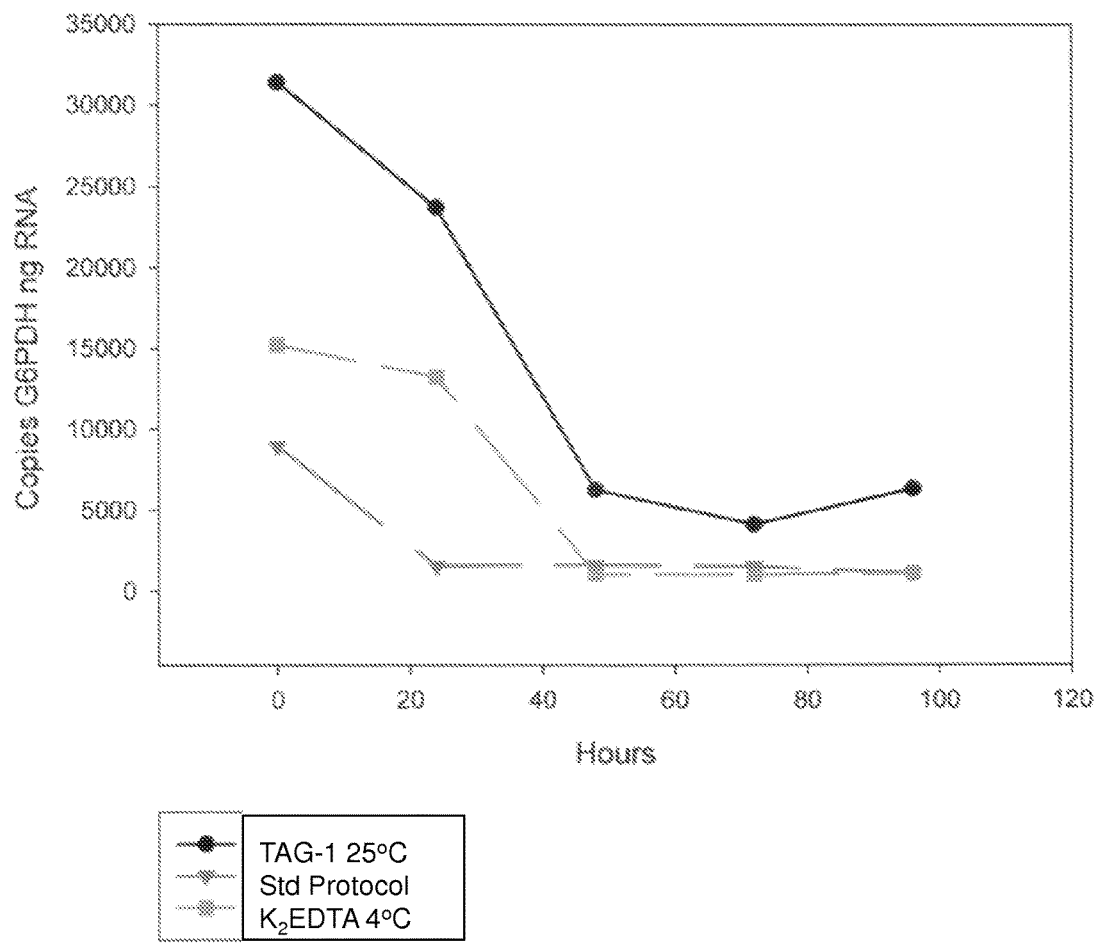
FIG. 4 is a graph of reverse transcriptase RT-PCR results of the PGK gene from aged LNCaP-FGC cells, comparing the use of one embodiment of the cell preserving reagent in accordance with the invention to conventional preserving reagents.
Figure 5:
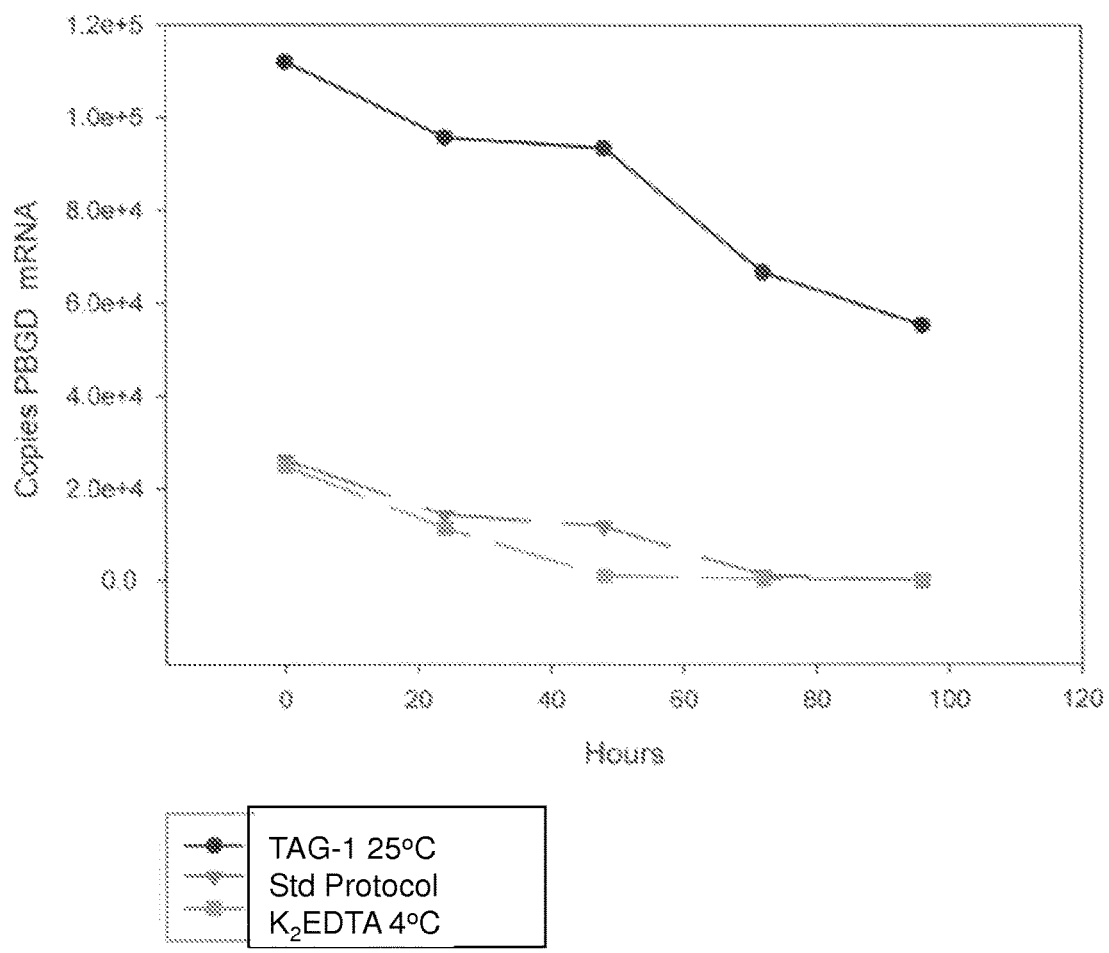
FIG. 5 is a graph of mRNA copies of the PBGD gene from aged PC3 cancer cells, comparing reverse transcriptase RT-PCR results of one embodiment of the cell preserving reagent in accordance with the invention to conventional reagents.

Example II is a study of one embodiment of the tissue cell preserving reagent effectiveness on preserving LNCaP-FGC cells and PC-3 cells. The results for preserving LNCaP-FGC cells in TAG-1 reagent compared to standard cell resuspension solutions are shown in FIG. 4. The results for preserving PC-3 cells in TAG-1 reagent compared to standard cell resuspension solutions are shown in FIG. 5.

The Human Prostate cell lines DU145, PC-3 and LNCaP-FGC were purchased from the American Type Collection (Manassas Va., USA). DU145 cells were cultured in DMEM media supplemented with 10% PBS plus Penicillin (100 units/mL) and Streptomycin (100 μL/mL). PC-3 and LNCaP-FGC cells were cultured in RPMI 1640 media supplemented with 10% fetal bovine serum (FBS) and Penicillin (100 units/mL) and Streptomycin (100 μL/mL). The cells were grown in tissue culture plates to a confluency of about 70%. The cells were then harvested by traditional methods and resuspended in one embodiment of the cell preserving reagent, TAG-1, or a control solution such as $K_2EDTA$, 20% Formalin, or Saline with Thimerosal.

The study using LNCaP-FGC cells compared the preservation effectiveness of TAG-1, a saline Thimerosal solution, and $K_2EDTA$ solution. The cells were resuspended in either TAG-1 or the control solutions and allowed to age for up to 100 hours. The TAG-1 solution was left at 25° C., while the $K_2EDTA$ solution was kept at 4° C. At various time points, 0 hr, 24 hr, 48 hr, 72 hr, and 100 hrs, the RNA was extracted from the aged cells to determine the integrity of the mRNA from each sample. FIG. 4 is a graph showing the comparison of the cancer cells aged in the TAG-1 reagent or the two control solutions. The copies of G6PDH mRNA were detected for each time point using RT-PCR. FIG. 4 shows that the TAG-1 solution kept the mRNA/cells viable better than the control solutions. The control solutions showed no copies of G6PDH at the 48 hr time point or even earlier. The TAG-1 solution was able to still have viable cells with intact mRNA even at 100 hours.

The study using PC-3 cells (FIG. 5) compared the preservation effectiveness of TAG-1, a saline/thimerosal solution, and $K_2EDTA$ solution. The cells were resuspended in either TAG-1 or the control solutions and allowed to age for up to 100 hours. The TAG-1 solution was left at 25° C., while the $K_2EDTA$ solution was kept at 4° C. At various time points, 0 hr, 24 hr, 48 hr, 72 hr, and 100 hrs, the RNA was extracted from the aged cells to determine the integrity of the mRNA from each sample. FIG. 5 is a graph showing the comparison of the cancer cells aged in the TAG-1 reagent or the two control solutions. The copies of PBGD mRNA were detected for each time point using RT-PCR. FIG. 5 shows that the TAG-1 solution kept the mRNA intact better than the control solutions. The control solutions showed almost no copies of PBGD at the 48 hr time point. The TAG-1 solution was able to still have viable cells with intact mRNA even at 100 hours.

The study using renal cancer cells compares one of the embodiments of the preserving reagent of the invention to two other solutions, one being 20% Formalin and the other being a $K_2$EDTA with Sodium Thiocyanate solution. The renal cancer cells were grown and harvested in a similar manner as the prostate cancer cell lines utilized above. The cells were then aged for up to 100 hours in either TAG-1, 20% Formalin, or the $K_2$EDTA with Sodium Thiocyanate solution.

Figure 6:
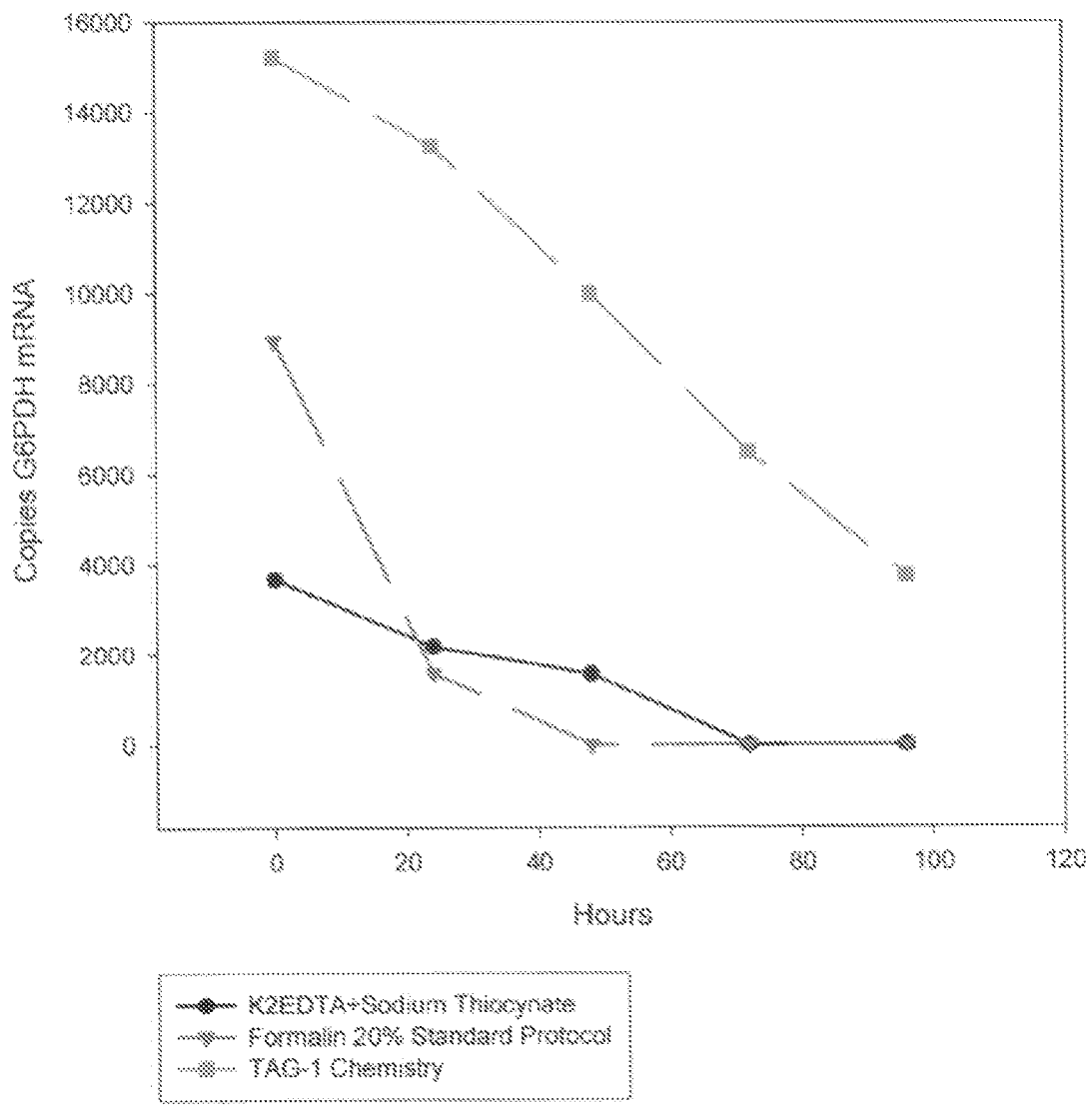
FIG. 6 is a graph of mRNA copies of G6PDH of various aged renal cancer cells, comparing the use of one embodiment of the preserving reagent to conventional preserving solutions.

FIG. 6 shows a graph of the copies of G6PDH mRNA in the aged renal cancer cells detected by RT-PCR over time (0 hr, 24 hr, 48 hr, 72 hr and 100 hr). The cells aged in the Formalin solution have no detectable copies of G6PDH at 48 hours and the cells aged in $K_2$EDTA plus sodium thiocyanate have no detectable mRNA G6PDH at 72 hours. The cells aged in the TAG-1 formulation still have mRNA detectable at 100 hours.

The TAG-1 formulation for these experiments comprised Leptin, α,α-Trehalose, Sodium Thiocyanate, EDTA, buffers, DMSO and Glycerol. Final concentrations of the formulation were Sodium Thiocyanate 0.01 M, EDTA 0.01 M, Glycerol 0.25 M, Buffers 0.001 M, Leptin 0.001 M, and α,α-Trehalose 0.20 M.

Example III

Figure 7:
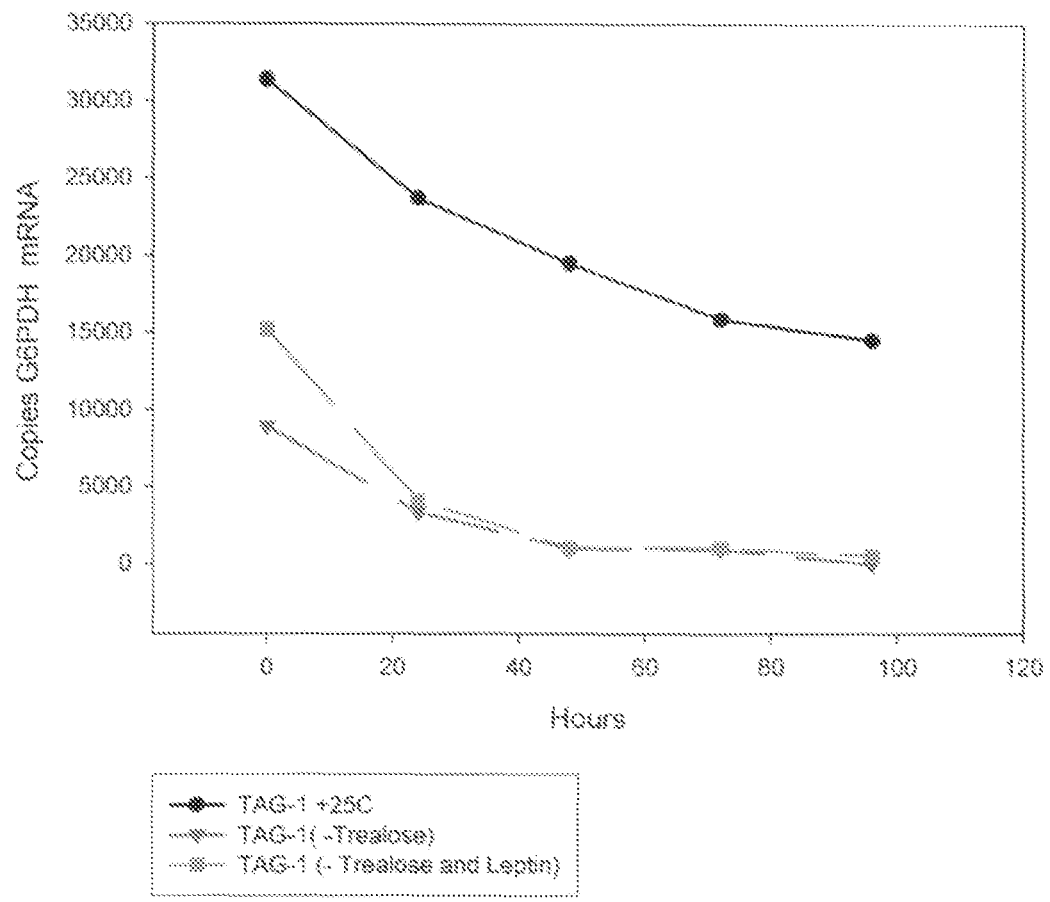
FIG. 7 is a graph comparing three different embodiments of the preserving reagent used on aged renal cancer cells.

Example III is a study showing the cell preservation effectiveness of having α,α-Trehalose and Leptin in one of the embodiments of the tissue cell preserving reagent in accordance with the invention. Renal cancer cells were used to compare the copies of G6PDH mRNA present over time (0 hr, 24 hr, 48 hr, 72 hr, and 100 hr) for three formulations, TAG-1, TAG-1 without α,α-Trehalose, and TAG-1 without α,α-Trehalose and Leptin. The samples were left at room temperature before extracting the mRNA from the renal cells. FIG. 7 shows a graph of the comparison of the three formulations of the number of copies of G6PDH mRNA is present after the renal cancer cells have been aged (resuspended in the preserving solution) in one of the three cell preserving reagent solutions. FIG. 7 clearly shows the effectiveness of having both α,α-Trehalose and Leptin in the cell preserving formulation. TAG-1 without α,α-Trehalose and TAG-1 without α,α-Trehalose and Leptin show no copies of G6PDH mRNA at time point 48 hours, while mRNA G6PDH copies are detected in the cells resuspended in the TAG-1 formulation even at the 100 hour time point.

The TAG-1 formulation for these experiments comprised Leptin, α,α-Trehalose, Sodium Thiocyanate, EDTA, buffers, DMSO, and Glycerol. Final concentrations of the formulation were Sodium Thiocyanate 0.01 M, EDTA 0.01 M, Glycerol 0.25 M, Buffers 0.001 M, Leptin 0.001 M, and α,α-Trehalose 0.20 M.

Example IV

Example IV is a microarray study comparing gene expression patterns of liquid nitrogen ($LN_2$) flash frozen tissue to tissue kept in one embodiment of the invention, the TAG-1 cell preserving formulation. The mRNA gene expression was completed on a Roche array 4-plex, 19K genes. The Array hybridization and scanning was performed through the Roche internal gene expression service using mRNA from Ishikawa cancer cells provided by Truckee Applied Genomics. The results were analyzed by extracting fluorescence from the array after alignment using quartile normalization. Gene calls were generated using the Robust Multichip Average (RMA) algorithm. Pairwise comparisons were visualized on scatter plots, and all treatments were compared by hierarchical clustering, both standard methods for array data visualization. Array quality control was achieved by comparing expression distributions across 10 arrays with no apparent outliers.

Table IV below, shows the microarray experimental design. Tissue was either aged in TAG-1 or stored for the specified time in $LN_2$.

TABLE IV

|  | 0 hr | 24 hr | 48 hr | 72 hr | 96 hr |
| --- | --- | --- | --- | --- | --- |
| TAG-1 | N = 1 | N = 1 | N = 1 | N = 1 | N = 1 |
| $LN_2$ | N = 1 | N = 1 | N = 1 | N = 1 | N = 1 |

The pairwise correlation matrix is shown below in Table V in tabular and graphical form. The experimental groups clustered with themselves, and in general showed good internal correlation.

TABLE V

|  | LN2 0 hr | LN2 24 hr | LN2 48 hr | LN2 72 hr | LN2 96 hr | TAG 0 hr | TAG 24 hr | TAG 48 hr | TAG 72 hr | TAG 96 hr |
| --- | --- | --- | --- | --- | --- | --- | --- | --- | --- | --- |
| LN2 0 hr | 1 | 0.987 | 0.984 | 0.981 | 0.975 | 0.971 | 0.94 | 0.922 | 0.873 | 0.89 |
| LN2 24 hr | 0.987 | 1 | 0.99 | 0.991 | 0.982 | 0.974 | 0.951 | 0.929 | 0.881 | 0.895 |
| LN2 48 hr | 0.984 | 0.99 | 1 | 0.992 | 0.984 | 0.97 | 0.947 | 0.925 | 0.876 | 0.891 |
| LN2 72 hr | 0.981 | 0.991 | 0.992 | 1 | 0.986 | 0.966 | 0.946 | 0.926 | 0.877 | 0.892 |
| LN2 96 hr | 0.975 | 0.982 | 0.984 | 0.986 | 1 | 0.954 | 0.94 | 0.918 | 0.886 | 0.897 |
| TAG 0 hr | 0.971 | 0.974 | 0.97 | 0.966 | 0.954 | 1 | 0.96 | 0.934 | 0.871 | 0.885 |
| TAG 24 hr | 0.94 | 0.951 | 0.947 | 0.946 | 0.94 | 0.96 | 1 | 0.97 | 0.918 | 0.926 |
| TAG 48 hr | 0.922 | 0.929 | 0.925 | 0.926 | 0.918 | 0.934 | 0.97 | 1 | 0.951 | 0.965 |

TABLE V-continued

|  | LN2 0 hr | LN2 24 hr | LN2 48 hr | LN2 72 hr | LN2 96 hr | TAG 0 hr | TAG 24 hr | TAG 48 hr | TAG 72 hr | TAG 96 hr |
|---|---|---|---|---|---|---|---|---|---|---|
| TAG 72 hr | 0.873 | 0.881 | 0.876 | 0.877 | 0.886 | 0.871 | 0.918 | 0.951 | 1 | 0.982 |
| TAG 96 hr | 0.89 | 0.895 | 0.891 | 0.892 | 0.897 | 0.885 | 0.926 | 0.965 | 0.982 | 1 |

Regression Models:

For each of the 24,000 genes and each of the two experimental groups, a linear regression model was fit, with time as the independent variable and expression as the dependent variable. The model yielded a slope and an associated p-value for each gene. The slopes and p-values are summarized in Table VI below.

TABLE VI

|  | Genes P < .05 | Genes P < .01 | Genes P < .001 |
|---|---|---|---|
| TAG-1 | 5811 | 1696 | 197 |
| LN2 | 3101 | 786 | 85 |
| Intersection | 825 | 66 | 0 |

|  | Genes P < .05 Slope > 0 | Genes P < .05 Slope < 0 | Genes P < .05 Total |
|---|---|---|---|
| TAG-1 | 2597 | 3214 | 5811 |
| LN2 | 1541 | 1560 | 3101 |

| | Absolute Slope, All Genes (Median, First to Third Quartile) |
|---|---|
| TAG-1 | .13 (.09 to .23) |
| LN2 | .09 (.04 to .15) |

Units for slope = log2 expression units per day

| | Absolute Slope, All Genes (Median, First to Third Quartile) |
|---|---|
| TAG-1 | 7% (6% to 13.1%) |
| LN2 | 6% (3% to 11%) |

Units for slope = percent change per day

Variation Across Time:

For each of the 24,000 genes and each of the two experimental groups, the standard deviation and coefficient of variation across the five time points was computed, see TABLE VII below. These results were consistent with the regression model results shown in TABLE VI above.

TABLE VII

|  | Gene Time Standard Deviation Median (First to Third Quartile) | Gene Time Coefficient of Variation Median (First to Third Quartile) |
|---|---|---|
| TAG-1 | 0.484 (0.210 to 0.421) | 32.8% (15.0% to 28.1%) |
| LN2 | 0.277 (0.199 to 0.376) | 19.0% (13.7% to 25.7%) |

Mean differences of the two sets are shown in TABLE VIII below. Overall, while there were significant mean difference between the groups, LN2 and TAG-1, the differences were well balanced between positive and negative differences.

Freezing tissues in liquid nitrogen is the gold standard for keeping cellular tissue intact. The above experiments compare the effectiveness of storing tissue in TAG-1 vs. liquid nitrogen. The above results indicate that the gene expression did not over or under express in cells stored in TAG-1 compared to those stored in liquid nitrogen, indicating that TAG-1, over the time period tested was comparable to liquid nitrogen storage in preserving cellular integrity at the gene expression level.

The TAG-1 formulation for these experiments comprised Leptin, α,α-Trehalose, Sodium Thiocyanate, EDTA, buffers, DMSO and Glycerol. Final concentrations of the formulation were Sodium Thiocyanate 0.01 M, EDTA 0.01 M, Glycerol 0.25 M, Buffers 0.001 M, Leptin 0.001 M, and α,α-Trehalose 0.20 M.

Example V

Example V is a study to evaluate media performance in ex vivo bladder and prostate cancer slice tissue cultures. Bladder and prostate tumor tissues are stored for various lengths of time at room temperature in one embodiment of the invention, TAG-1. Slice viability over time is evaluated by examination of tissue morphology with standard microscopy, MTT assay for cell viability, TUNEL assay for apoptosis, and Ki67 assessment of proliferation using immunostaining. Gene expression array experiments will also be included in the assessment of the viability of the cancer tissues.

Comparisons will be made of slice cultures using a membrane system in which tissue slices (400-800 microns thick) will be maintained via access to TAG-1 across a membrane covering a well. The optimized protocol with TAG-1 will be tested on chemotherapy drugs and clinical samples.

The general methodology comprises obtaining bladder and prostate cancer tissue samples from NSG-PDX JAX mice or patient cancer biopsy cores. Tissue will be processed either as slices or as cut blocks, and cultured on culture plates in a 3D matrix or on a membrane. Normal tissue slices from same patients will serve as controls to determine the differences in behavior of cancer and normal tissue. In addition, isolated peripheral blood mononuclear cells (PBMC) will be analyzed for their correlation to tumor cell behavior. Tissue samples are assayed at various time intervals for up to eight days in standard saline/thimerosal solutions, $K_2$EDTA solution and TAG-1 for comparison of TAG-1 to standard storage protocols.

The TAG-1 formulation for these experiments comprised Leptin, α,α-Trehalose, Sodium Thiocyanate, EDTA, buffers, DMSO, and Glycerol. Final concentrations of the formulation were Sodium Thiocyanate 0.01 M, EDTA 0.01 M, Glycerol 0.25 M, Buffers 0.001 M, Leptin 0.001 M, and α,α-Trehalose 0.20 M.

It is to be understood that the detailed description of illustrative embodiments are provided for illustrative purposes. The scope of the claims is not limited to these specific embodiments or examples. Therefore, various process limitations, elements, details, and uses can differ from those just described, or be expanded on or implemented using technologies not yet commercially viable, and yet still be within the inventive concepts of the present disclosure. The scope of the invention is determined by the following claims and their legal equivalents.

The invention claimed is:

1. A method of preserving a biological sample by contacting the biological sample with a cell preservation reagent, the cell preservation reagent comprising:
   a) a chelator; and
   b) leptin,
   wherein the biological sample comprises a solid tumor, and
   wherein the biological sample is preserved for at least 72 hours after contacting the biological sample with the cell preservation reagent.

2. The method of claim 1, further comprising:
   performing a gene expression analysis on the biological sample.

3. The method of claim 2, wherein the performing the gene expression analysis comprises measuring quantities of RNA transcribed from one or more genes in the biological sample.

4. The method of claim 3, wherein quantities of RNA transcribed from one or more genes in the biological sample are measured using PCR.

5. The method of claim 3, wherein quantities of RNA transcribed from one or more genes in the biological sample are measured using sequencing.

6. The method of claim 2, wherein the performing the gene expression analysis comprises measuring quantities of proteins in the biological sample.

7. The method of claim 2, further comprising:
   generating a gene expression profile based on the gene expression analysis.

8. The method of claim 1, wherein gene expression levels of the biological sample after contacting the biological sample with the cell preservation reagent are within 50% of gene expression levels of the biological sample before the contacting.

9. The method of claim 1, wherein the biological sample is a surgically excised cancer tissue sample.

10. The method of claim 1, wherein preserving the biological sample comprises maintaining viable gene expression components within the biological sample.

11. The method of claim 1, wherein the cell preservation reagent comprises a concentration of leptin that is from about 0.001 M to about 2 M.

12. The method of claim 1, wherein the chelator is selected from the group consisting of EDTA, EGTA, and BAPTA.

13. The method of claim 1, wherein the cell preservation reagent further comprises a buffer that is selected from the group consisting of BIS-TRIS, BIS-TRIS Propane, HEPES, MES, MOPS, and Sodium Phosphate Buffer.

14. The method of claim 1, wherein the biological sample is preserved for up to 96 hours after contacting the biological sample with the cell preservation reagent.

15. The method of claim 1, wherein the biological sample is preserved for up to 120 hours after contacting the biological sample with the cell preservation reagent.

16. The method of claim 1, wherein the cell preservation reagent is a homogenous solution.

17. A method of preserving a biological sample by contacting the biological sample with a cell preservation reagent, the cell preservation reagent comprising:
   a) a chelator;
   b) a kosmotrope, wherein the kosmotrope comprises α,α-trehalose; and
   c) leptin,
   wherein the biological sample comprises a surgically excised cancer tissue sample.

18. The method of claim 17, wherein the cell preservation reagent continuously contacts the biological sample for at least 72 hours, and wherein gene expression levels of the biological sample after the continuously contacting the biological sample with the cell preservation reagent for at least 72 hours are within 50% of gene expression levels of the biological sample before the continuously contacting.

19. The method of claim 17, wherein the cell preservation reagent continuously contacts the biological sample for at least 96 hours, and wherein gene expression levels of the biological sample after the continuously contacting the biological sample with the cell preservation reagent for at least 96 hours are within 50% of gene expression levels of the biological sample before the continuously contacting.

20. A method of preserving a biological sample by contacting the biological sample with a cell preservation reagent, the cell preservation reagent comprising:
   a) a chelator; and
   b) leptin,
   wherein the biological sample comprises a solid tumor, and
   wherein a concentration of the leptin is between about 0.001 M to about 2 M.

21. The method of claim 20, further comprising:
   performing a gene expression analysis on the biological sample.

22. The method of claim 20, wherein the biological sample is a surgically excised cancer tissue sample.

23. The method of claim 20, wherein the chelator is selected from the group consisting of EDTA, EGTA, and BAPTA.

24. The method of claim 20, wherein the cell preservation reagent further comprises a buffer that is selected from the group consisting of BIS-TRIS, BIS-TRIS Propane, HEPES, MES, MOPS, and Sodium Phosphate Buffer.

25. A method of preserving a biological sample by contacting the biological sample with a cell preservation reagent, the cell preservation reagent comprising:
   a) a chelator; and
   b) leptin,
   wherein the biological sample comprises a solid tumor, and
   wherein the chelator is selected from the group consisting of EDTA, EGTA, and BAPTA.

26. The method of claim 25, further comprising:
   performing a gene expression analysis on the biological sample.

27. The method of claim 25, wherein the biological sample is a surgically excised cancer tissue sample.

28. The method of claim 25, wherein the cell preservation reagent further comprises a buffer that is selected from the group consisting of BIS-TRIS, BIS-TRIS Propane, HEPES, MES, MOPS, and Sodium Phosphate Buffer.

29. A method of preserving a biological sample by contacting the biological sample with a cell preservation reagent, the cell preservation reagent comprising:
   a) a chelator; and
   b) leptin,
   wherein the biological sample comprises a solid tumor,
   wherein the biological sample is preserved for at least 72 hours after contacting the biological sample with the cell preservation reagent,
   wherein a concentration of the leptin is between about 0.001 M to about 2 M, and wherein the chelator is selected from the group consisting of EDTA, EGTA, and BAPTA.

30. The method of claim 29, further comprising:
performing a gene expression analysis on the biological sample.

31. The method of claim 29, wherein the biological sample is a surgically excised cancer tissue sample.

32. The method of claim 29, wherein the cell preservation reagent further comprises a buffer that is selected from the group consisting of BIS-TRIS, BIS-TRIS Propane, HEPES, MES, MOPS, and Sodium Phosphate Buffer.

* * * * *